United States Patent
Newman

(10) Patent No.: US 7,788,054 B2
(45) Date of Patent: Aug. 31, 2010

(54) METHOD AND SYSTEM FOR CALIBRATING A TUBE SCANNER

(75) Inventor: Frederic M. Newman, Midland, TX (US)

(73) Assignee: Key Energy Services, LLC, Houston, TX (US)

( * ) Notice: Subject to any disclaimer, the term of this patent is extended or adjusted under 35 U.S.C. 154(b) by 593 days.

(21) Appl. No.: 11/691,163

(22) Filed: Mar. 26, 2007

(65) Prior Publication Data

US 2007/0227225 A1 Oct. 4, 2007

Related U.S. Application Data

(60) Provisional application No. 60/786,661, filed on Mar. 28, 2006.

(51) Int. Cl.
  *G01B 21/30* (2006.01)
(52) U.S. Cl. .............. 702/85; 73/1.01; 73/1.89; 73/152.57; 702/35; 702/103
(58) Field of Classification Search ............ 73/1.01, 73/1.89, 152.01, 152.54, 152.57, 86, 618, 73/865.9; 422/53; 436/6; 702/35–36, 38, 702/40, 85, 103
See application file for complete search history.

(56) References Cited

U.S. PATENT DOCUMENTS

| | | | | |
|---|---|---|---|---|
| 3,569,708 A | * | 3/1971 | Weinbaum et al. ............ 378/90 |
| 4,393,485 A | | 7/1983 | Redden ................... 367/25 |
| 4,545,017 A | | 10/1985 | Richardson ................ 702/9 |
| 4,660,419 A | | 4/1987 | Derkacs et al. ............. 73/622 |
| 4,700,142 A | | 10/1987 | Kuckes ................ 340/853.5 |
| 4,779,201 A | | 10/1988 | Iizuka et al. ............... 702/10 |
| 4,851,773 A | | 7/1989 | Rothstein ................ 324/220 |
| 5,043,663 A | | 8/1991 | Lam ................... 324/242 |
| 5,051,962 A | | 9/1991 | Eaton ................... 367/33 |

(Continued)

FOREIGN PATENT DOCUMENTS

GB 2027373 A * 2/1980 ............ 72/49

(Continued)

OTHER PUBLICATIONS

PCT/US07/64964 International Search Report and Written Opinion of the International Searching Authority, or Declaration—Date of mailing Feb. 22, 2008.

(Continued)

*Primary Examiner*—Thomas P Noland
(74) *Attorney, Agent, or Firm*—King & Spalding LLP

(57) ABSTRACT

A scanner instrument used for scanning tubing that is being placed into an oil well or being removed from the oil well can be calibrated during retrieval of tubing from the well. Calibrating the tube scanner includes scanning a tubing standard and comparing the data from the standard scan to the known characteristics of the standard. The relationship between the scanned data and the known characteristics can be computed. The relationship between the scanned data and the known characteristics can be used as the calibration function for the scanner. Calibrating the tube scanner can also include scanning a string of tubing segments and then adjusting the data collected. The adjustment is based upon equalizing the data peaks that occur in the scan data at the coupling joints between tube segments.

15 Claims, 7 Drawing Sheets

U.S. PATENT DOCUMENTS

| | | | |
|---|---|---|---|
| 5,193,628 A | 3/1993 | Hill et al. | 175/45 |
| 5,218,301 A | 6/1993 | Kuckes | 324/346 |
| 5,237,539 A | 8/1993 | Selman | 367/69 |
| 5,278,549 A | 1/1994 | Crawford | 340/853.2 |
| 5,491,668 A | 2/1996 | Priest | 367/35 |
| 5,548,900 A | 8/1996 | Hunt-Grubbe | 33/302 |
| 5,626,192 A | 5/1997 | Connell et al. | 166/255.1 |
| 5,678,643 A | 10/1997 | Robbins et al. | 175/45 |
| 5,744,952 A * | 4/1998 | Latham et al. | 324/207.16 |
| 5,947,213 A | 9/1999 | Angle et al. | 175/24 |
| 6,021,093 A | 2/2000 | Birchak | |
| 6,079,490 A | 6/2000 | Newman | |
| 6,209,639 B1 | 4/2001 | Newman | 166/250.01 |
| 6,285,955 B1 | 9/2001 | Goldwasser | 702/6 |
| 6,316,937 B1 | 11/2001 | Edens | 324/220 |
| 6,347,292 B1 | 2/2002 | Denny et al. | 702/188 |
| 6,359,434 B1 | 3/2002 | Winslow et al. | 324/220 |
| 6,377,189 B1 | 4/2002 | Newman | 340/854.6 |
| 6,411,084 B1 | 6/2002 | Yoo | 324/221 |
| 6,571,634 B1 | 6/2003 | Bazarov et al. | 73/623 |
| 6,728,638 B2 | 4/2004 | Newman | |
| 6,760,665 B1 | 7/2004 | Francis | 702/6 |
| 6,896,056 B2 | 5/2005 | Mendez et al. | 166/254.2 |
| 7,006,920 B2 | 2/2006 | Neman et al. | 702/6 |
| 7,571,054 B2 * | 8/2009 | Newman | 702/6 |
| 2004/0226712 A1 | 11/2004 | Hood | |
| 2005/0024055 A1 * | 2/2005 | Cavaluzzi et al. | 324/321 |
| 2005/0194182 A1 | 9/2005 | Rodney et al. | 175/24 |
| 2005/0267686 A1 | 12/2005 | Ward | 702/6 |
| 2006/0047430 A1 | 3/2006 | Edwards | 702/6 |
| 2008/0035335 A1 * | 2/2008 | Newman | 166/250.01 |

FOREIGN PATENT DOCUMENTS

| | | | | |
|---|---|---|---|---|
| JP | 61070455 A * | 4/1986 | | 73/620 |
| JP | 63238498 A * | 10/1988 | | |
| WO | WO 2004/074808 A2 | 9/2004 | | |

OTHER PUBLICATIONS

PCT/US07/64948 International Search Report and Written Opinion of the International Searching Authority, or Declaration—Date of mailing Dec. 17, 2007.

PCT/US07/64894 International Search Report and Written Opinion of the International Searching Authority, or Declaration—Date of mailing Feb. 7, 2008.

PCT/US07/65032 International Search Report and Written Opinion of the International Searching Authority, or Declaration—Date of mailing Jul. 2, 2008.

PCT/US07/64846 International Search Report and Written Opinion of the International Searching Authority, or Declaration—Date of mailing Dec. 12, 2007.

* cited by examiner

METHOD AND SYSTEM FOR CALIBRATING A TUBE SCANNER

This application claims benefit of U.S. Provisional Application Ser. No. 60/786,661, filed on Mar. 28, 2006.

FIELD OF THE INVENTION

The present invention relates generally to a scanner instrument for collecting and analyzing data describing a tube associated with an oil well and relates more specifically to calibration of the scanner instrument.

BACKGROUND

During the drilling, completion and maintenance of an oil well, personnel routinely insert and/or extract devices such as tubing, tubes, pipes, rods, hollow cylinders, casing, conduit, collars, and duct into the well. For example, a service crew may use a workover rig or service rig to extract a string of tubing and sucker rods from a well that has been producing petroleum. The crew may inspect the extracted tubing and evaluate whether one or more sections of that tubing should be replaced due to physical wear, thinning of the tubing wall, chemical attack, pitting, or other defect. The crew typically replaces sections that exhibit an unacceptable level of wear and makes note of other sections that are beginning to show wear and may need replacement at a subsequent service call.

As an alternative to manually inspecting tubing, the service crew may deploy an instrument to evaluate the tubing as the tubing is extracted from the well and/or inserted into the well. The scanning instrument typically remains stationary at the wellhead, and the workover rig moves the tubing through the instrument's measurement zone. This instrument may be called a "tube scanner".

The tube scanner typically measures pitting and wall thickness and can identify cracks in the tubing wall. Radiation, field strength (electrical, electromagnetic, or magnetic), and/or fluid pressure differential may interrogate the tubing to evaluate these wear parameters. The tube scanner typically produces a raw analog signal and outputs a sampled or digital version of that analog signal.

In other words, the tube scanner typically stimulates a section of the tubing using a field, radiation, or pressure and detects the tubing's interaction with or response to the stimulus. An element, such as a transducer, converts the response into an analog electrical signal. For example, the tube scanner may create a magnetic field into which the tubing is disposed, and the transducer may detect changes or perturbations in the field resulting from the presence of the tubing and any anomalies of that tubing.

The analog electrical signal output by the transducer can have an arbitrary or essentially unlimited number of states or measurement possibilities. That is, rather than having two discrete or binary levels, typical transducers produce signals that can assume any of numerous levels or values. As the tubing passes through the measurement filed of the instrument, the analog transducer signal varies in response to variations and anomalies in the wall of the moving tubing.

The tube scanner also typically includes a system, such as an analog-to-digital converter ("ADC"), that converts the analog transducer signal into one or more digital signals suited for reception and display by a computer. These digital signals typically provide a "snapshot" of the transducer signal. Thus, the ADC typically outputs a number, or set of a numbers, that represents or describes the analog transducer signal at a certain instant in time. Because the analog transducer signal describes the section of tubing that is in the tube scanner's measurement zone, the digital signal is effectively a sample or a snapshot of a parameter-of-interest of that tubing section.

The signals generated by the tube scanner may fluctuate or drift over time. Vibrations or mechanical shocks that occur during transportation of the instrument may slightly alter the performance of the tube scanner. Thermal variance, power fluctuations, or vibrations during the operation of the tube scanner may cause drift or noise in the readings output by the tube scanner. These fluctuation, drift, and noise components of the signals output from the tube scanner may lead to inconsistencies of the type that would result in two different tube scanner outputs from scanning the same pipe at two different times. Such inconsistencies are undesirable when the tube scanner outputs are used for evaluating the wear and wear patterns of the tubing and determining if particular sections of tubing should be retained for reuse or otherwise discarded.

To address these representative deficiencies in the art, an improved capability for calibrating the tube scanner is needed. A need also exists for a capability of an oilfield service crew to calibrate the tube scanner in the field. A further need exists for a capability to use one or more post-operational calibrations to correct, validate, or flag the data scanned during the operation of the tube scanner.

SUMMARY OF THE INVENTION

The present invention relates to a method for calibrating a scanner instrument used for scanning tubing that is being placed into an oil well or being removed from the well. This scanning instrument may be called a "tube scanner". In one aspect of the present invention, a method for calibration of the tube scanner may involve scanning a tubing standard with known characteristics and then computing the relationship between the data from the scan and the known characteristics of the tubing standard. This relationship between the expected and actual data may then be used as the calibration function of the tube scanner.

In another aspect of the present invention, a method for calibration of the tube scanner may include adjusting the data collected while scanning a string of tube segments based on equalizing the data peaks that occur in the scan data at the coupling joints between tube segments.

In yet another aspect of the present invention, the dependence of the results of a tube scan upon the speed at which the tube moves through the scanner is determined. The inventive tube scanner calibration may establish typical, fast limit, and slow limit metrics for the speed at which a tube should be moved through a tube scanner. The typical speed would be the one where the calibrated scanner reproduces expected scan values most closely and the fast limit and slow limit would be the scan speeds where the tube scanner still operates within tolerances, but movement of tubing through the tube scanner that is faster that the fast limit or slower than the slow limit may introduce excessive error into the scan. These limit values can be used by the crew to guide their operation of the rig while extracting or inserting tubing through the tube scanner.

The discussion of tube scanner calibration presented in this summary is for illustrative purposes only. Various aspects of the present invention may be more clearly understood and appreciated from a review of the following detailed description of the disclosed embodiments and by reference to the drawings and any claims that may follow. Moreover, other aspects, systems, methods, features, advantages, and objects of the present invention will become apparent to one with skill in the art upon examination of the following drawings and detailed description. It is intended that all such aspects, systems, methods, features, advantages, and objects are to be included within this description, are to be within the scope of the present invention, and are to be protected by any accompanying claims.

Figure 1:
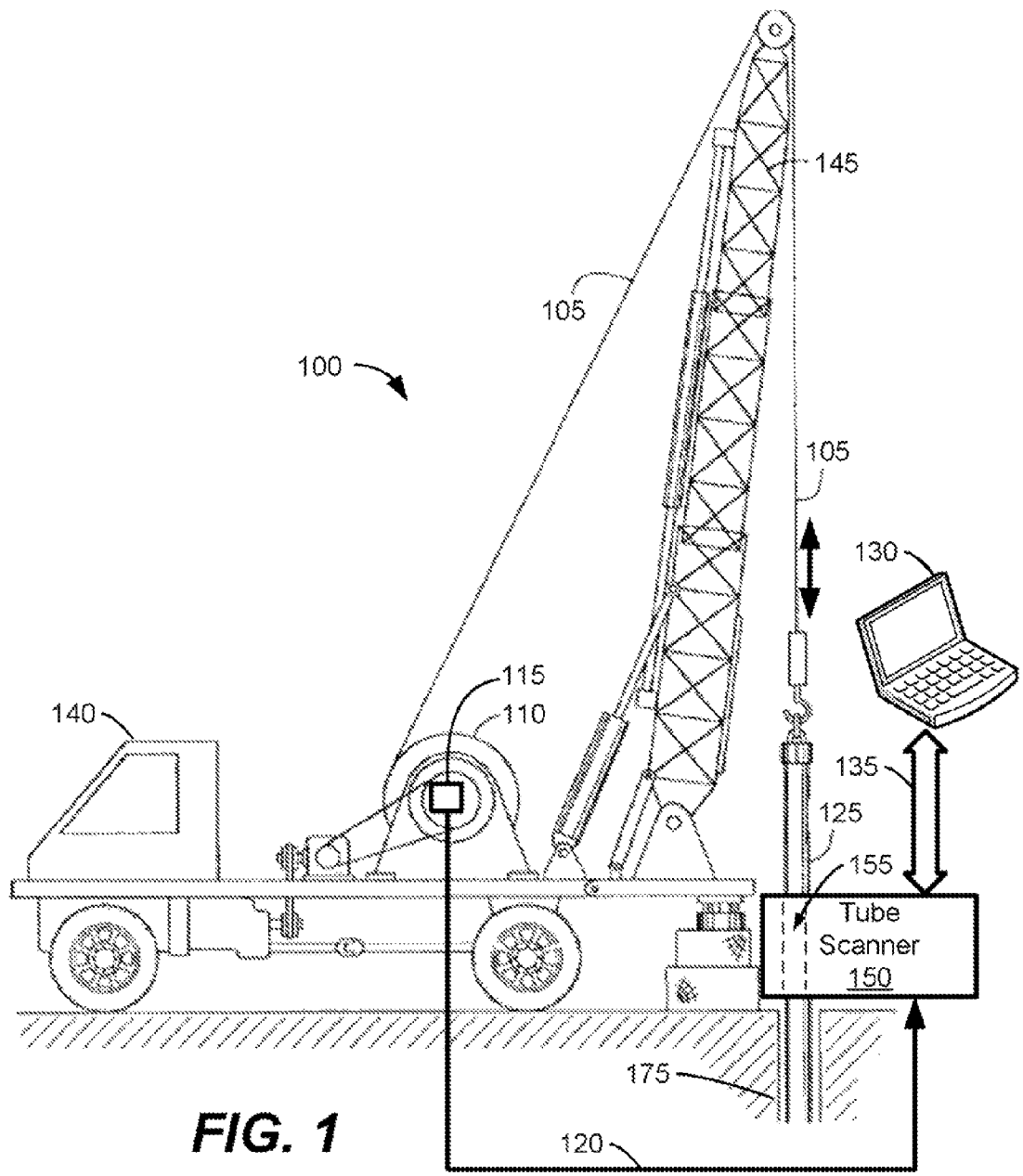
FIG. 1 is an illustration of an exemplary system for servicing an oil well where the system scans tubing as the tubing is extracted from or inserted into the well in accordance with an exemplary embodiment of the present invention.

Many aspects of the present invention can be better understood with reference to the above drawings. The components in the drawings are not necessarily to scale, emphasis instead being placed upon clearly illustrating the principles of exemplary embodiments of the present invention. Moreover, in the drawings, reference numerals designate like or corresponding, but not necessarily identical, elements throughout the several views.

DETAILED DESCRIPTION OF EXEMPLARY EMBODIMENTS

Figure 2:
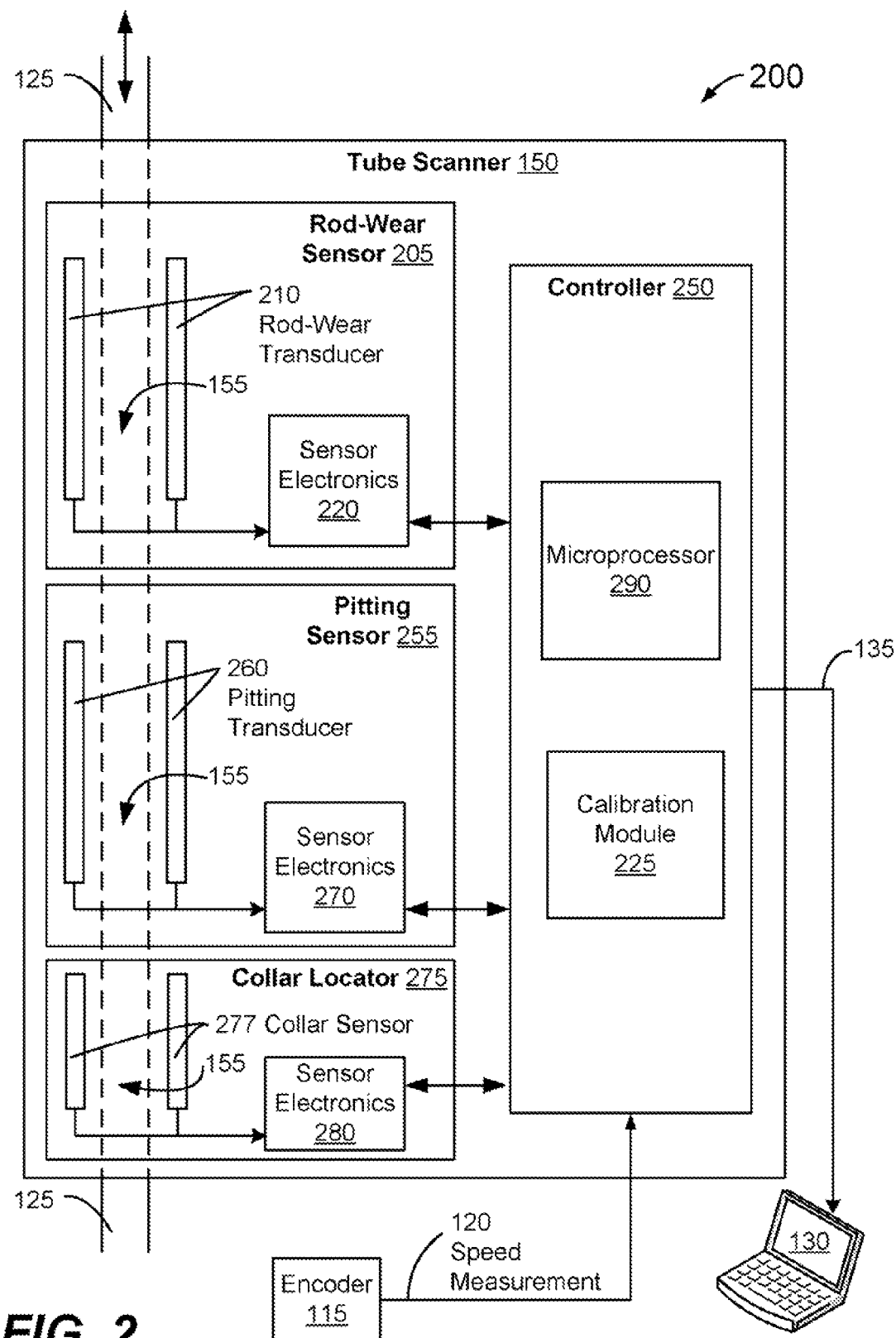
FIG. 2 is a functional block diagram of an exemplary system for scanning tubing that is being inserted into or extracted from an oil well in accordance with an exemplary embodiment of the present invention.
Figure 4:
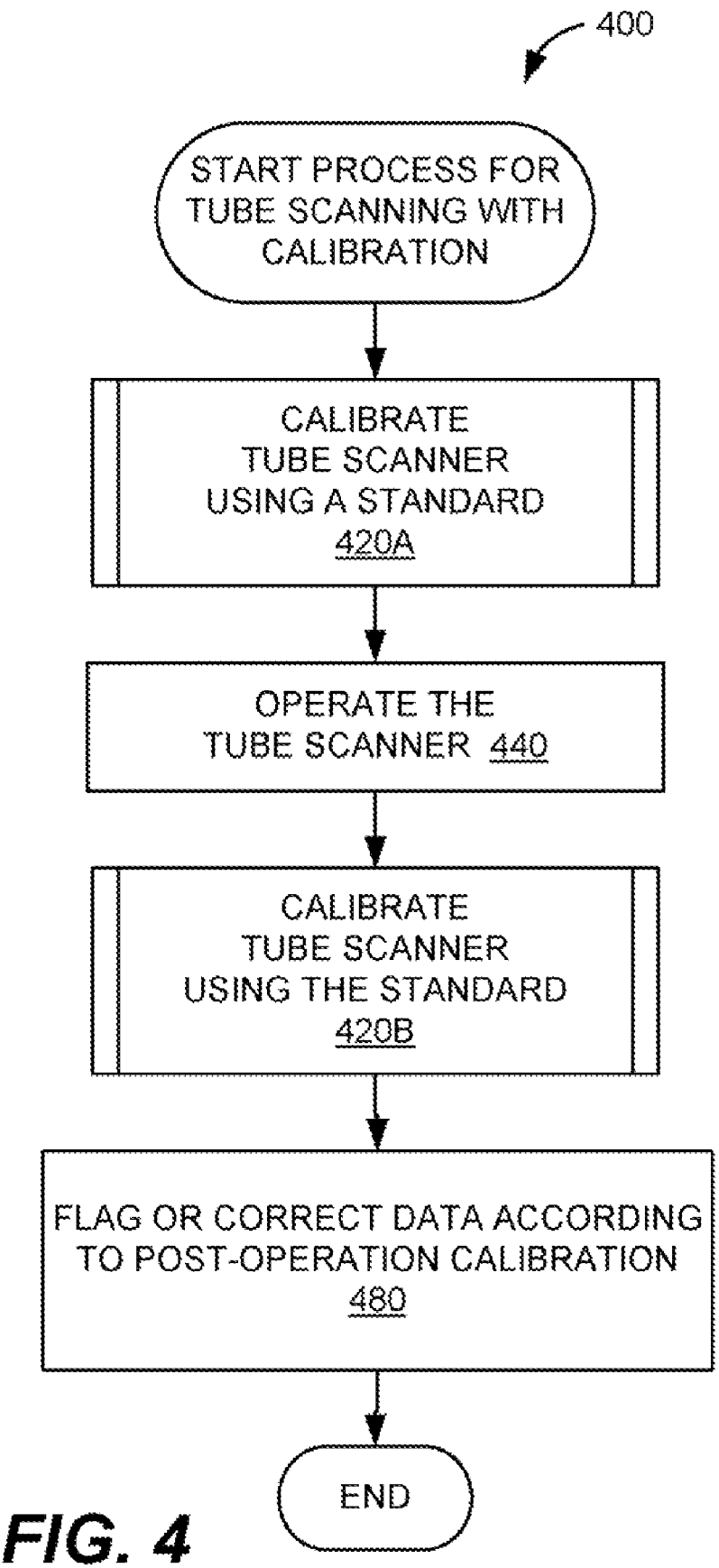
FIG. 4 is a flowchart of an exemplary process for scanning tubing that is being inserted into or extracted from an oil well and for calibrating the tube scanner using a tube standard in accordance with an exemplary embodiment of the present invention.
Figure 5:
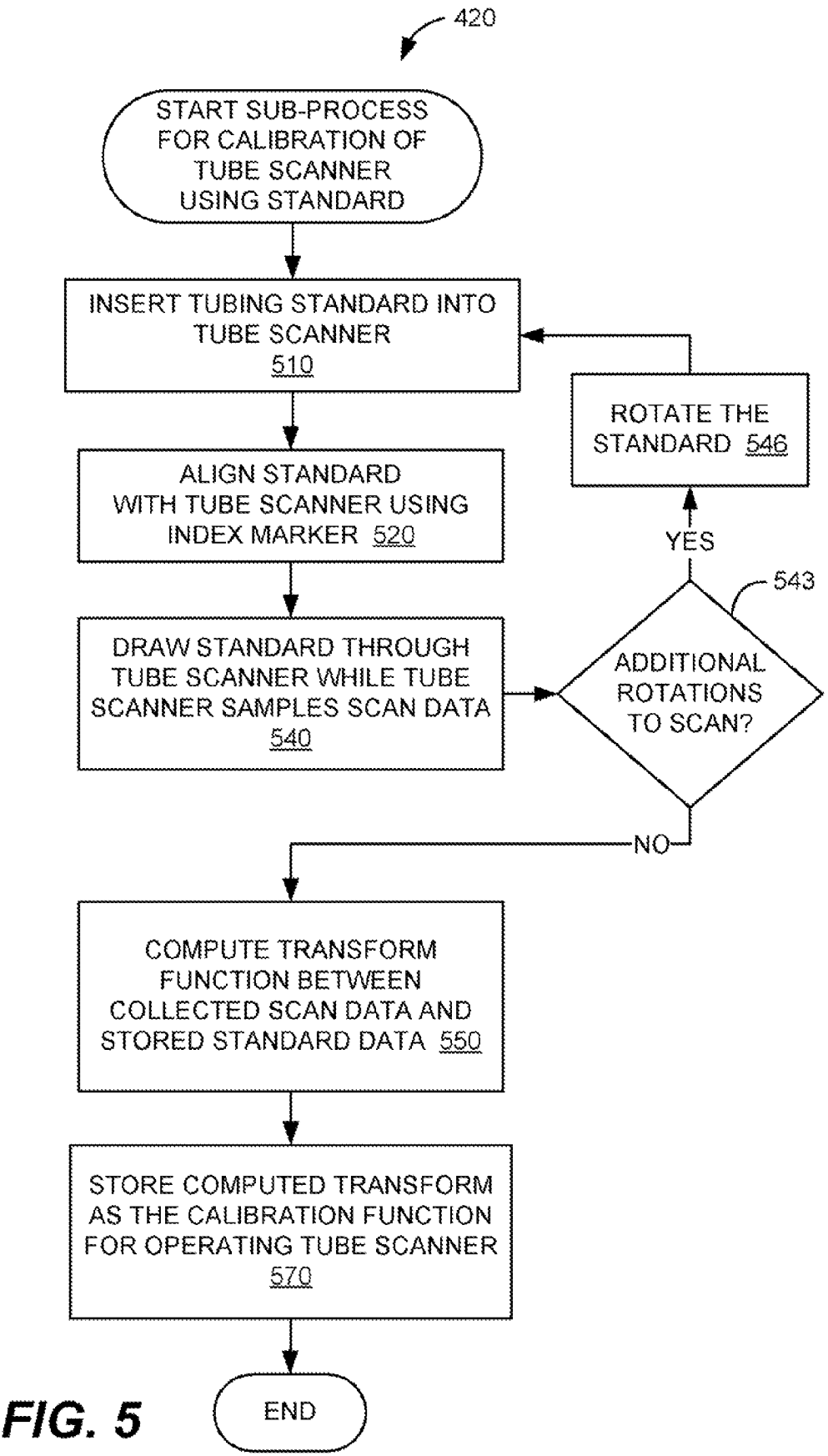
FIG. 5 is a flowchart of an exemplary process for calibrating a tube scanner using a tube standard and stored information about the standard in accordance with an exemplary embodiment of the present invention.
Figure 6:
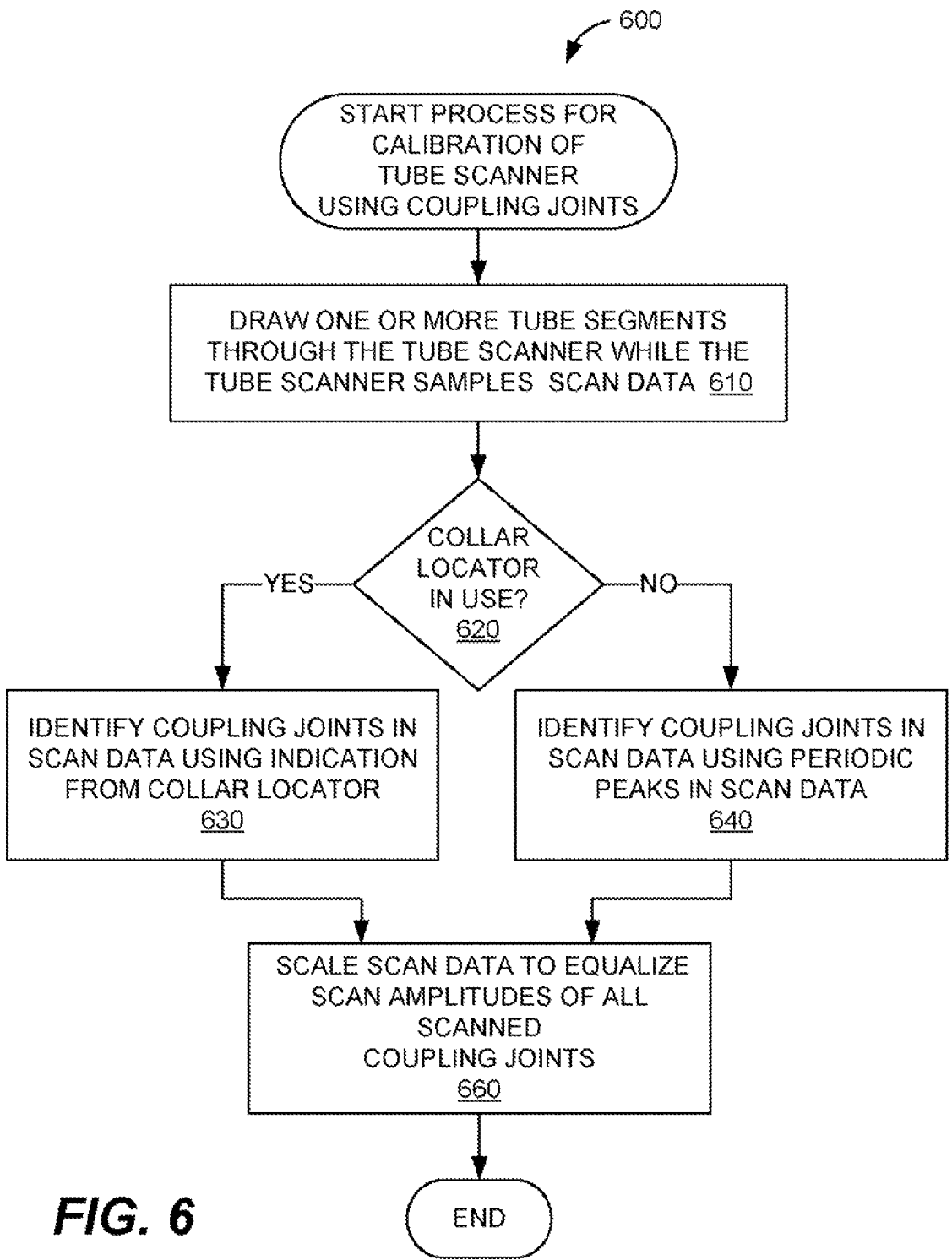
FIG. 6 is a flowchart of an exemplary process for scanning tubing that is being inserted into or extracted from an oil well and for calibrating the tube scanner based on the scanned information in accordance with an exemplary embodiment of the present invention.

The present invention supports a method for calibrating a tube scanner used to scan tubing being placed into or being removed from a well. An exemplary method and system for calibrating the tube scanner will now be described more fully hereinafter with reference to FIGS. 1-6. These figures show representative embodiments of the present invention. FIG. 1 depicts a workover rig moving tubing through a tube scanner in a representative operating environment for one embodiment of the present invention. FIG. 2 provides a block diagram of a tube scanner that monitors, senses, or characterizes tubing and that validates and interprets tubing data. FIG. 3 depicts an exemplary tubing standard for calibrating the tube scanner illustrated in FIG. 2. FIGS. 4, 5 and 6 provide flow diagrams of methods for calibrating a tube scanning instrument.

The invention can be embodied in many different forms and should not be construed as limited to the embodiments set forth herein; rather, these embodiments are provided so that this disclosure will be thorough and complete, and will fully convey the scope of the invention to one having ordinary skill in the art. Furthermore, all "examples" or "exemplary embodiments" given herein are intended to be non-limiting, and among others supported by representations of the present invention.

Moreover, although an exemplary embodiment of the invention is described with respect to calibrating a tube scanner in a measurement zone adjacent to a wellhead, one skilled in the art will recognize that the invention may be employed or utilized in connection with a variety of applications in the oilfield or another operating environment.

FIG. 1 illustrates a system 100 for servicing an oil well 175. The system 100 scans the tubing 125 as the tubing 125 is extracted from or inserted into the well 175 according to an exemplary embodiment of the present invention.

The oil well 175 includes a hole bored or drilled into the ground to reach an oil-bearing formation. The borehole of the well 175 is encased by a tube or pipe (not explicitly shown in FIG. 1), known as a "casing," that is cemented to down-hole formations and that protects the well from unwanted fluids and debris within the formation.

Within the casing is a tube 125 that carries oil, gas, hydrocarbons, petroleum products, and/or other formation fluids, such as water, to the surface. In operation, a sucker rod string (not explicitly shown in FIG. 1), disposed within the tube 125, forces the oil uphole. Driven by strokes from an uphole machine, such as a "rocking" pump jack, the sucker rod moves up and down to communicate reciprocal motion to a down-hole pump (not explicitly shown in FIG. 1). With each stroke, the downhole pump moves oil up the tube 125 towards the wellhead.

As shown in FIG. 1, a service crew uses a workover or service rig 140 to service the well 175. During the illustrated procedure, the crew pulls the tubing 125 from the well, for example to repair or replace the downhole pump. The tubing 125 includes a string of sections, each of which may be referred to as a "joint," that typically range in length from 29 to 34 feet (about 8.8 to 10.3 meters). The joints screw together via collars, unions, tubing joints, or threaded connections.

The crew uses the workover rig 140 to extract the tubing 125 in increments or steps, typically two joints per increment. The rig 140 includes a derrick or boom 145 and a cable 105 that the crew temporarily fastens to the tubing string 125. A motor-driven reel 110, drum, winch, or block and tackle pulls the cable 105 thereby hoisting or lifting the tubing string 125 attached thereto. The crew lifts the tubing string 125 a vertical distance that approximately equals the height of the derrick 145, typically about sixty feet or two joints.

More specifically, the crew attaches the cable 105 to the tubing string 125, which is vertically stationary during the attachment procedure. The crew then lifts the tubing 125, generally in a continuous motion, so that two joints are extracted from the well 175 while the portion of the tubing string 125 below those two joints remains in the well 175. When those two joints are out of the well 175, the operator of the reel 110 stops the cable 105, thereby halting upward motion of the tubing 125. The crew then separates or unscrews the two exposed joints from the remainder of the tubing string 125 that extends into the well 175. A clamping apparatus grasps the tubing string 125 while the crew unscrews the two exposed joints, thereby preventing the string 125 from dropping into the well 175 when those joints separate from the main string 125.

The crew repeats the process of lifting and separating two-joint sections of tubing from the well 175 and arranges the extracted sections in a stack of vertically disposed joints, known as a "stand" of tubing. After extracting the full tubing string 125 from the well 175 and servicing the pump, the crew reverses the step-wise tube-extraction process to place the tubing string 125 back in the well 175. In other words, the crew uses the rig 140 to reconstitute the tubing string 125 by threading or "making up" each joint and incrementally lowering the tubing string 125 into the well 175.

The system 100 incorporates a tube scanner for monitoring, scanning, assessing, or evaluating the tubing 125 as the tubing 125 moves into or out of the well 175. The tube scanner 150 obtains information or data bout the portion of the tubing 125 that is in the tube scanner's 150 sensing or measurement zone 155. Via a data link 120, an encoder 115 provides the tubing scanner 150 with speed, velocity, and/or positional information about the tube 125. For example, the encoder 115 may be mechanically linked to the reel 110 to determine motion and/or position of the tubing 125 as the tubing 125 moves through the measurement zone 155.

As an alternative to the illustrated encoder 115, some other form of positional or speed sensor can determine the derrick's block speed or the rig engine's rotational velocity in revolutions per minute ("RPM"), for example.

Another data link 135 connects the tube scanner 150 to a computing device or computer 130, which can be a laptop, a handheld, personal digital assistant ("PDA"), a cellular system, a portable radio, a personal messaging system, a wireless appliance, or a stationary personal computer ("PC"), for example. The computer 130 displays data that the tube scanner 150 has obtained from the tubing 125. The computer 130 can present the tubing data graphically, for example in a trend format. The service crew monitors or observes the displayed data on the computer 130 or other display device to evaluate the condition of the tubing 125. The service crew can thereby grade the tubing 125 according to its fitness for continued service, for example.

The communication link 135 can include a direct link or a portion of a broader communication network that carries information among other devices or similar systems to the system 100. Moreover, the communication link 135 can include a path through the Internet, an intranet, a private network, a telephone network, an Internet protocol ("IP") network, a packet-switched network, a circuit-switched network, a local area network ("LAN"), a wide area network ("WAN"), a metropolitan area network ("MAN"), the public switched telephone network ("PSTN"), a wireless network, or a cellular system, for example. The communication link 135 can also include a signal path that is optical, fiber optic, wired, wireless, wire-line, waveguided, or satellite-based, to name a few possibilities. Signals transmitting over the link 135 can carry or convey data or information digitally or via analog transmission. Such signals can include modulated electrical, optical, microwave, radiofrequency, ultrasonic, or electromagnetic energy, among other energy forms.

The computer 130 typically includes hardware and software. That hardware may include various computer components, such as disk storage, disk drives, microphones, random access memory ("RAM"), read only memory ("ROM"), one or more microprocessors, power supplies, a video controller, a system bus, a display monitor, a communication interface, and input devices. Further, the computer 130 can include a digital controller, a microprocessor, or some other implementation of digital logic, for example.

The computer 130 executes software that may include an operating system and one or more software modules for managing data. The operating system can be the software product that Microsoft Corporation of Redmond, Wash. sells under the registered trademark WINDOWS, for example. The data management module can store, sort, and organize data and can also provide a capability of graphing, plotting, charting, or trending data. The data management module can be or include the software product that Microsoft Corporation sells under the registered trademark EXCEL, for example.

In one exemplary embodiment of the present invention, a multitasking computer functions as the computer 130. Multiple programs can execute in an overlapping timeframe or in a manner that appears concurrent or simultaneous to a human observer. Multitasking operation can include time slicing or timesharing, for example.

The data management module can include one or more computer programs or pieces of computer executable code. To name a few examples, the data management module can include one or more of a utility, a module or object of code, a software program, an interactive program, a "plug-in" an "applet," a script, a "scriptlet," an operating system, a browser, an object handler, a standalone program, a language, a program that is not a standalone program, a program that runs a computer, a program that performs maintenance or general purpose chores, a program that is launched to enable a machine or human user to interact with data, a program that creates or is used to create another program, and a program that assists a user in the performance of a task such as database interaction, work processing, accounting, or file management.

Turning now to FIG. 2, this figure illustrates a functional block diagram of an instrumentation system 200 for scanning tubing 125 that is being inserted into or extracted from an oil well 175 according to one exemplary embodiment of the present invention. One skilled in the information-technology, computing, signal processing, sensor, or electronics arts will recognize that the components and functions that are illustrated as individual blocks in FIG. 2, and referenced as such elsewhere herein, are not necessarily strictly separate modules. Furthermore, the contents of each block are not necessarily positioned in one physical location. In one embodiment of the present invention, certain blocks represent virtual modules, and the components, data, and functions may be physically dispersed. Moreover, in some exemplary embodiments, a single physical device may perform two or more functions that FIG. 2 illustrates in two or more distinct blocks. For example, the function of the computer 130 can be integrated into the tubing scanner 150 to provide a unitary or commonly-housed hardware and software element that acquires and processes data and displays processed data in graphical form for viewing by an operator, technician, or engineer.

The tubing scanner 150 may include a rod-wear sensor 205 and a pitting sensor 255 for determining parameters relevant to continued use of the tubing 125. The rod-wear sensor 205 assesses relatively large tubing defects or features such as wall thinning. Wall thinning may be due to physical wear or abrasion between the tubing 125 and the sucker rod that is reciprocates therein, for example. Meanwhile, the pitting sensor 255 detects or identifies smaller defects or features, such as pitting that stems from corrosion or some other form of chemical attack within the well 175. These small flaws may be visible to the naked eye or may have microscopic features, for example. Pitting can occur on the inside surface of the tubing 125, the so-called "inner diameter," or on the outside of the tubing 125.

The inclusion of the rod-wear sensor 205 and the pitting sensor 255 in the tubing scanner 150 is intended to be illustrative rather than limiting. The tube scanner 150 can include additional sensors or measuring apparatus that may be suited to a particular application. For example, the instrumentation system 200 can include a collar locator 275, a device that detects tubing cracks or splits, a temperature gauge, a camera, a hydrostatic tester, etc. In one exemplary embodiment of the present invention, the tube scanner 150 includes or is coupled to an inventory counter, such as one of the inventory counting devices disclosed in U.S. Patent Application Publication Number 2004/0196032.

The tube scanner 150 also includes a controller 250 that may process signals from the rod-wear sensor 205 and the pitting sensor 255. In one exemplary embodiment, the controller 250 processes signals according to a speed measurement 120 from the encoder 115. The controller 250 can include a computer, a microprocessor 290, a computing device, or some other implementation of programmable or hardwired digital logic. In one exemplary embodiment, the controller 250 includes one or more application specific integrated circuits ("ASICS") or digital signal processing ("DSP") chips. Calibration module 225 may include executable code stored on ROM, programmable ROM ("PROM"), RAM, an optical disk, a hard drive, magnetic media, tape, paper, or some other machine readable medium. Alternatively, calibration module 225 maybe implemented in programmable or hardwired electronics, or some combination of hardware and executable software code.

The speed measurement 120 from the encoder 115 may be used in one aspect of calibrating tube scanner 150 that relates to the dependence of the results of a tube scan upon the speed 120 at which the tube moves through the tube scanner 150. The calibration module 225 may establish typical, fast limit, and slow limit metrics for the speed at which a tube 125 should be moved through a tube scanner 150. The typical speed would be the one where the calibrated tube scanner 150 reproduces expected scan values most closely and the fast limit and slow limit would be the scan speeds where the tube scanner 150 still operates within tolerances, but movement of tubing 125 through the tube scanner 150 that is faster that the fast limit or slower than the slow limit may introduce excessive error into the scan. These limit values can be used by the crew to guide their operation of the rig 140 while extracting or inserting tubing 125 through the tube scanner 150.

The rod-wear sensor 205 may include a transducer 210 that outputs an electrical signal containing information about the section of tubing 125 that is in the measurement zone 155. Sensor electronics 220 may amplify, condition, and digitize the output from transducer 210 and then provide controller 250 with samples or snapshots of the wall thickness of the portion of the tubing 125 that is situated in the measurement zone 155.

Similar to the rod-wear sensor 205, the pitting sensor 255 include a pitting transducer 260. Sensor electronics 270 may amplify, condition, and digitize the output from transducer 260 and then provide controller 250 with samples or snapshots of the amount and nature of pitting in the walls of the portion of the tubing 125 that is situated in the measurement zone 155.

The transducers, such as 210 and 260 may respond to stimuli within the measurement zone 155 such as electromagnetic, mechanical, fluid pressure differential, sonic, ultrasonic, or optical/visual.

A collar locator 275 includes a collar sensor 277 and sensor electronics 280. The sensor 277 may include a mechanical switch, electromagnetic transducer, optical detector, or other sensor for identifying when a coupling joint collar is within measurement zone 155. Sensor electronics 280 may amplify, condition, and digitize the output from sensor 277 and then provide controller 250 with information regarding the presence of a coupling joint collar within the measurement zone 155. Inclusion of collar locator 275 in tube scanner 150 or even outside of the tube scanner 150 but as part of service rig system 100, can provide controller 250 and/or computer 130 with information regarding the location of couplings or collars at the points where tube 125 sections or joints connect to one another within the tubing string.

The calibration module 225 can use signals from sensors, such as 205 and 255, and indications from the operating crew as inputs to one or more calibration processes. These calibration processes can determine corrective calibration functions that may transform the signals output by the sensors, such as 205 and 255, to more accurately represent signals that are descriptive of the actual tube 125 being scanned. These calibration functions may be required due to drift, offset, noise, or other errors or artifacts introduced into the signals from sensors, such as 205 and 255. Once these calibration functions are determined, the calibration module 225 of controller 250 may apply the calibration functions to the signals received from sensors, such as 205 and 255, in order to achieve data that is more representative of the actual tube 125 being analyzed. One of ordinary skill in the art will appreciate that the calibration functionality, described for one exemplary embodiment as a calibration module 225 of controller 250, may, without departing from the scope or spirit of the present invention, be located and/or partitioned otherwise, for example a functionality of computer 130, controller 250, or electronics within sensors, such as 205 or 255. An exemplary tubing standard for use in calibration as well as some exemplary calibration process flowcharts are described hereinafter.

Figure 3A:
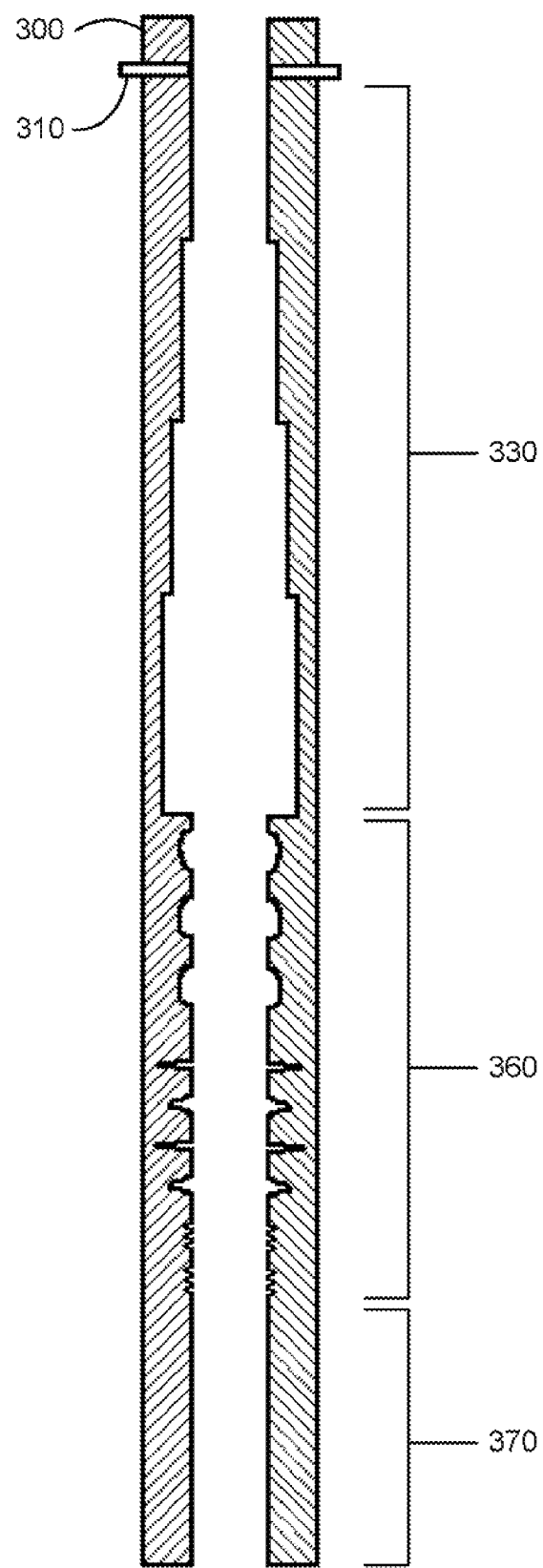
FIG. 3A illustrates a vertical cross-section of an exemplary tube standard for use in calibrating a tube scanner in accordance with an exemplary embodiment of the present invention.

FIG. 3A illustrates a vertical cross-section of an exemplary tubing standard 300 used to calibrate the tube scanner 150 of FIGS. 1 and 2. Referring now to FIGS. 2 and 3A, the exemplary standard 300 can be manufactured with a known set of physical characteristics. The standard 300 may thus be expected to stimulate sensors 205, 255 inside of tube scanner 150 to produce known response signals according to the known physical properties of the tubing standard 300. This can be considered the "expected scan" of standard 300. When the tube scanner 150 is used to scan the standard 300, the resulting signals from the sensors 205, 255 can be considered the "actual scan" of the standard 300 by those sensors 205, 255 at that time. Deviation between the "expected scan" and the "actual scan" represents the drift, offset, error, noise, artifacts, or other aberration exhibited by the sensors 205, 255 within the tube scanner 150. This deviation is what is sought to be removed, or substantially minimized, by the application of a calibration function by the calibration module 225.

A region 330 of the standard 300 having various wall thicknesses may be used to exercise and calibrate the rod-wear sensor 205. A region 360 of the standard 300 having various depths, widths, and structures of wall-pitting features or grooves may be used to exercise and calibrate the pitting sensor 255. While regions 330 and 360 of the tubing standard 300 may be substantially circularly symmetrical, region 370 of the tubing standard 300 may contain vertical features or grooves which introduce a rotational aspect to the tubing standard 300. Thus the expected scan of the tubing standard 300 will differ as a function of the angle at which tubing standard 300 is drawn through tube scanner 150. This rotationally variant tube region 370 is discussed in more detail below and illustrated in FIG. 3B.

When inserted into the tube scanner 150 for calibration purposes, the standard 300 may be aligned using an index marker 310. The index marker 310 allows the standard 300 to be scanned in a consistent manner that is beneficial to the calibration process because the actual scan can be synchronized with, or matched up to, the expected scan more readily.

The index marker 310 may be painted onto, molded or machined into, or externally affixed to the standard 300. One skilled in the mechanical or manufacturing arts will appreciate various other embodiments of the index marker 310, the use of which would not depart from the scope or spirit of the invention. Additionally, the standard 300 may be operated without alignment via the index marker 310 and synchronization may be achieved by controller 250 or computer 130 using correlation to match up expected features of the standard 300 as identified within the scan data.

Figure 3B:
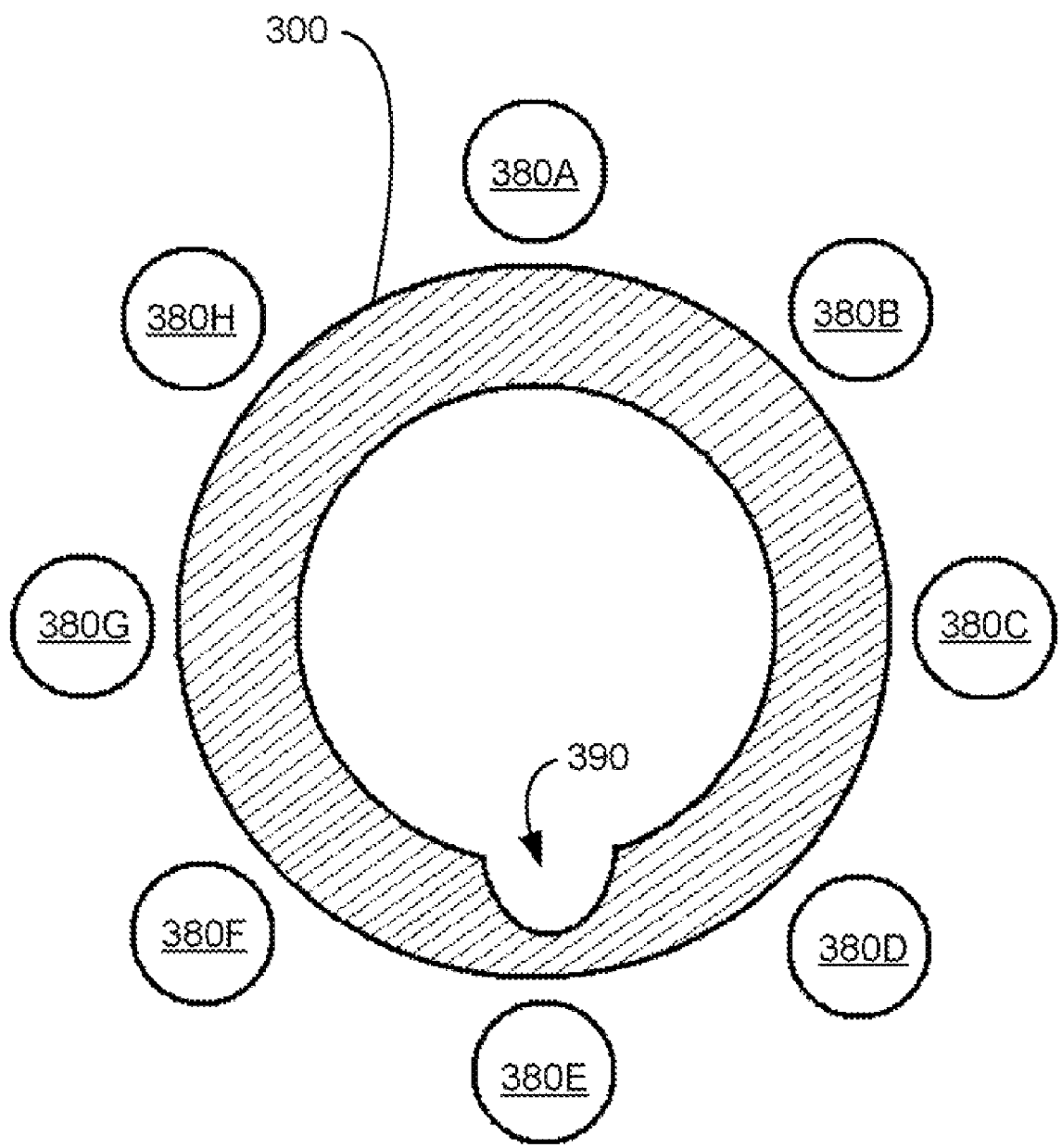
FIG. 3B illustrates a horizontal cross-section of the rotationally variant region of an exemplary tube standard disposed within a circular array of transducer elements in accordance with an exemplary embodiment of the present invention.

FIG. 3B illustrates a horizontal cross-section of the rotationally variant region 370 of an exemplary tubing standard 300 disposed with a circular array of transducer elements 380A-H. Referring now to FIGS. 2, 3A and 3B, the rotational aspect region 370 of exemplary standard 300 can be manufactured with vertical features or grooves 390. These vertical grooves 390 introduce a rotationally variant scan of the standard 300 in the region 370 of rotational variance. This is in contrast to regions 330 and 360 of tubing standard 300 which may substantially display circular symmetry. Sensor transducers, such as 210 and 260 shown in FIG. 2 may be physically arranged as an array of transducer elements 380A-H disposed around the measurement zone 155. Vertical grooves 390 in tubing standard 300 may be used to isolate the response of each of the transducer elements 380A-H. For example, in the orientation illustrated in FIG. 3B, the groove 390 would be detected as a thinner wall measurement at transducer element 380E compared to the other seven transducer elements 380A-D, 380F-H. However if the tubing standard 300 were being inserted or extracted at an orientation rotated ninety degrees clockwise (as viewed in FIG. 3B) then groove 390 would be detected by transducer 380G. This rotational variance in the scan of region 370 of tubing standard 300 may be used to individually calibrate the sensor elements 380A-H circularly disposed around the measurement zone 155. Rotational variance in the scan of region 370 of the tubing standard 300 may also be used to identify individually malfunctioning or faulty sensor elements 380A-H. Further exploitation of these rotational variances in the calibration scanning are elaborated in the process flowchart illustrated in FIG. 5 below.

The physical design of the tubing standard 300 is specifically intended to represent features spanning the full range of pits, grooves and wall thickness that are measurable by the sensors 205, 255 within the tube scanner 150. When used as a calibration standard, these varied qualities may allow the tube scanner 150 to be calibrated over its full domain of operation. The two sensors 205, 255 of the tube scanner 150 are intended to be exemplary and not limiting. The tube scanner 150 may include other tube scanning sensors in various combinations without departing from the spirit or scope of the present invention. Similarly, the circular disposition of sensor elements 380A-H is intended to be exemplary and non-limiting. Sensor arrays of more or less than eight elements or arrangements other than the circular example may be employed within tube scanner 150 without departing from the spirit or scope of the present invention.

Processes for an exemplary embodiment of the present invention will be discussed below with reference to FIGS. 4, 5 and 6. An exemplary embodiment of the present invention can include one ore more computer programs or computer-implemented methods that implement functions or steps described herein and illustrated in the exemplary flowcharts of FIGS. 4, 5 and 6. However, it should be apparent that there could be many different ways of implementing the invention in computer programming, and the invention should not be construed as limited to any one set of computer program instructions. Further, a skilled programmer would be able to write such a computer program to implement the disclosed invention without difficulty based on the exemplary system architectures and flowcharts and the associated description in the application text, for example.

Therefore, disclosure of a particular set of program code instructions is not considered necessary for an adequate understanding of how to make and use the invention. The inventive functionality of any claimed process, method, or computer program will be explained in more detail in the following description in conjunction with the remaining figures illustrating representative functions and program flow.

Certain steps in the processes described below must naturally precede others for the present invention to function as described. However, the present invention is not limited to the order of the steps described if such order or sequence does not alter the functionality of the present invention in an undesirable manner. That is, it is recognized that some steps may be performed before or after other steps or in parallel with other steps without departing from the scope and spirit of the present invention.

Turning now to FIG. 4, this figure illustrates a flowchart of an exemplary process 400 for scanning tubing that is being inserted into or extracted from an oil well 175 and for calibrating the tube scanner 150 using a tube standard 300 within the operating environment of the exemplary workover rig 140 and tube scanner 150 of FIGS. 1 and 2. Now referring to FIGS. 1, 2 and 4, the exemplary method 400 begins at the START step and proceeds to step 420A where an oil field service crew calibrates the tube scanner 150 using the tubing standard 300. This calibration is elaborated below in sub-process 420 of FIG. 5.

At step 440, the crew operates the tube scanner 150. Operating the tube scanner 150 may include scanning tube segments 125 being extracted from, or inserted into, the well 175. Scanning tube segments 125 typically includes collecting, within controller 250, computer 130, or both, the digitized signals from sensor electronics, such as 220 or 270. Mechanical speed, velocity, or positional information may also be collected from the encoder 115. This mechanical information may assist in relating the collected sensor data with the physical area of tubing 125 being sampled and each snap-shot. The calibration module 225 may, in real-time, apply the calibration function obtained during the initial calibration 420A to the scan data collected during the scanner operation in step 440.

At step 420B, the crew calibrates the tube scanner 150 using the tubing standard 300. This calibration is elaborated below in sub-process 420 of FIG. 5. At step 480, the calibration module 225 may use this post-operation calibration to validate that the tube scanner 150 is still in calibration and was thus likely to have remained in calibration throughout the tube scanning operation of step 440. If the post-operational calibration 420B indicates that the tube scanner 150 has drifted out of calibration, the calibration module 225 may adjust the data collected during the tube scanning operation in step 440 according to the new calibration or the calibration module 225 may simply flag the data collected during the tube scanning operation in step 440 to be examined more closely in light of the post-operation calibration 420B.

Process 400 may provide for improved data collection during tube scanning operation 440 since the tube scanner 150 is calibrated in step 420A just prior to being operated and the calibrated again in step 420B just after operation. After the post-operational calibration, the calibration module 225 may verify that the tube scanner 150 is still in calibration and it may react accordingly if tube scanner 150 has drifted out of calibration. It should be appreciated that in addition to this exemplary embodiment where calibration occurs before operation and after operation, the calibration steps may take place one or more times during the operation of the tube scanner 150 at the same well without departing from the spirit of scope of the present invention. Such interspersed scanner calibration can be employed in the field when, for example, the service crew has an increased need for scan accuracy, or is concerned that the tube scanner 150 is not maintaining calibration for extended periods of operation due to, for example, vibrations or thermal fluctuations.

Turning now to FIG. 5, this figure illustrates a flowchart of an exemplary sub-process 420 for calibrating a tube scanner 150 using a tube standard 300 and stored information about the standard. This exemplary sub-process elaborates the steps described in the calibration steps 420A and 420B of FIG. 4.

At step 510, the oil field service crew inserts tubing calibration standard 300 into tube scanner 150. At step 520 the tubing standard 300 is aligned with the tube scanner 150 using the index marker 310 of tubing standard 300. Once the standard 300 is aligned into the tube scanner 150, the process proceeds at step 540 where the crew draws the calibration tubing standard 300 through the tube scanner 150 while the tube scanner 150 samples scan data describing the tubing standard 300. This scan data may be considered the "actual scan" in contrast to stored information describing the known physical characteristics of standard 300. This stored information may be considered the "expected scan" as it represents an idealization of what tube scanner 150 would, when perfectly calibrated, scan from the standard tubing 300.

At decision step 543, it is determined if additional partial rotations of tubing standard 300 are required. As discussed above and illustrated in FIG. 3B, partial rotation of the tubing standard 300 relates to the vertical feature 390 and to the isolation of individual transducer elements 380A-H within a sensor transducer (such as 210 or 260) arranged as a circular array. If the circular array of transducer elements 380A-H includes eight elements, as illustrated in FIG. 3B, and it is desirable to isolate each element than each partial rotation may be of 45 degrees and there may be seven such partial rotations interleaved between a total of eight scans of the tubing standard 300 through tube scanner 150. For varying numbers of circularly disposed transducer elements 380, the number of partial rotations and scans may be the same as the number of transducer elements 380 (as in the example just given). Alternatively, the number of partial rotations may be more or less than the number of transducer elements 380. Whatever the total number of partial rotations intended to fully exercise the tuber scanner 150, decision step 543 evaluates if the total number of partial rotations has been completed or if additional partial rotations are required to be scanned.

If decision step 543 determines that no additional partial rotations are required, then the "NO" branch is followed to step 550, otherwise, the "YES" branch is followed to step 546, where the partial rotation is carried out by the crew prior to beginning the next tube scan by returning to step 510. The amount of each partial rotation is, in the simplest preferred implementation, three hundred and sixty degrees divided by the total number of partial rotations. This approach would evenly space the partial rotation scans around the circle describing the horizontal cross-section of the measurement zone 155. Such even spacing of scans around the standard tubing 300 is exemplary and non-limiting. Other measures of partial rotation can be acceptable or even desirable.

At step 546, the crew may gauge the angle of the partial rotation using an external instrument, or by using angle markings on or within tube scanner 150, tubing standard 300, or index marker 310. The angle of partial rotation separating each scan of a rotational set may be entered or verified by the crew using the computer 130. This angular displacement information may be used by the calibration module 225 in making the calibration computations. After the first transition through step 543, the second and later passes through step 540 within the same rotational set of scans may be simplified to only include scanning the vertical feature region 370 of tubing standard 300 through the tube scanner 150. This simplification may be possible because only the vertical feature region 370 of the tubing standard 300 varies with rotational angle. Confining subsequent scans to this region 370 can reduce the total amount of time required to calibrate the tube scanner 150.

At step 550, calibration module 225 computes a transform that can act upon the actual scan to yield, or approximate, the expected scan. This transform can be considered a calibration function for the tube scanner 150. For example, if the values in the actual scan are all five less than the expected scan, then a calibration function may be to add five to all measured values. As a second example, if values in the actual scan are one third of those in the expected scan, a calibration function may be to multiply all measured values by three. These linear examples of calibration functions are intended to be exemplary and not limiting. One skilled in the control systems or signal processing arts will appreciate that the calibration function may be linear or nonlinear; may operate in time, frequency, phase, or other domain; may be static; or may be adaptive according to the minimization of one or more of various adaptation metrics without departing from the scope or spirit of the present invention.

At step 570, the transform, or calibration function, computed at step 550 may be stored for use by the calibration module 225 and may be applied to data scanned during operation of the tube scanner 150. Application of the calibration function to data scanned by the tube scanner 150 may remove, or reduce, deviation from the ideal operation of the tube scanner 150. Thus, tube scanner 150 may be considered to be calibrated. As such, operation of tube scanner 150 upon the tubing standard 300 would result in scan data substantially approximating the expected scan data. In this calibrated state, the tube scanner 150 may generate scan data during a scan of a tubing segment 125 that is substantially indicative of the actual physical properties of the tubing segment 125 and not including drift, noise, offset, or other artifact components to an extent that the scan data would be less useful for decision making regarding the tubing segment 125.

Turning now to FIG. 6, this figure illustrates a flowchart of an exemplary process 600 for calibrating a tube scanner 150 using coupling joints in a string of tubing 125. Instead of relying upon a calibration standard tubing 300, process 600 may use the scan data from the actual tubing 125 being operated upon by the tube scanner 150 to calibrate the tube scanner 150. It should be appreciated that tubing standard calibration, such as illustrated in processes 400 and 420 and coupling joint calibration, such as illustrated by process 600, are not mutually exclusive calibration techniques and they may be used in combination or alternatively at different phases of scanner operation.

Now referring to FIGS. 1, 2, and 6, the exemplary process 600 begins at step 610, where the tube segments being scanned are drawn, by the crew, through the tube scanner 150 while the tube scanner 150 collects, within controller 250, computer 130, or both, the digitized signals from sensor electronics, such as 220 or 270. Mechanical speed, velocity, or positional information may also be collected from the encoder 115. This mechanical information may assist in relating the collected sensor data with the physical area of tubing being sampled and each snap-shot.

At decision step 620, calibration module 225 determines whether or not a collar locator is in use. A collar locator 275 is an instrument that indicates when a coupling joint collar is being scanned. If a collar locator 275 is in use, the "YES" branch is followed to step 630, where the calibration module 225 uses the indications from the collar locator 275 to identify the coupling joints within the data scanned at step 610. If a collar locator 275 is not in use, the "NO" branch is followed to step 640 where the calibration module 225 identifies the coupling joints in the scan data using peaks in the data occurring at approximately thirty foot intervals. Each tubing segment is approximately thirty feet long and the scan data will peak, or saturate, at the times in the scan when a collar, or coupling joint, is passing within the measurement zone 155.

Once the coupling joints are identified within the scan data at either step 630 or 640, the process 600 continues to step 660 where the scan data is scaled up or down to equalize the scan amplitudes of all of the scanned coupling joints. Since the tube scanner 150 may saturate and provide a peak measurement at a coupling joint, scaling the data as to equalize all of the coupling joint regions may remove any drift errors introduced in the data during the scanning operation.

Using either the tubing standard process 400 (along with tubing standard 300) or the coupling joint equalization process 600, the present invention can calibrate a tube scanner 150. Use of such a calibrated tube scanner 150 can increase correctness and consistency in the scanning of tubing 125 over the use of a non-calibrated tube scanner. Correctness and consistency can benefit the art when the results of tube scans are used in making important decisions concerning whether or not a segment of tubing need be discarded due to excessive wear or in making decisions concerning the type and amounts of chemicals used in a well.

What is claimed is:

1. A method for calibrating a tubing scanner, comprising:
   inserting a tubing standard;
   scanning the tubing standard to produce a calibration scan;
   analyzing the calibration scan;
   computing a transform based on the calibration scan; and
   storing the transform for application to data obtained during the scanning of tubing.

2. The method of claim 1 further comprising
   optionally rotating and rescanning the tubing standard a plurality of times; and
   averaging the plurality of tubing standard scans to produce the calibration scan.

3. The method of claim 1 wherein the tubing standard has a first zone for calibration of a rod sensor.

4. The method of claim 1 wherein the tubing standard has a second zone for calibration of a pitting sensor.

5. The method of claim 1 further comprising comparing the calibration scan to a stored scan and computing the transform based on differences between the calibration scan and the stored scan.

6. The method of claim 1 further comprising analyzing the calibration scan and determining a rate of scanning based on a maximum peak height and a baseline.

7. A method for scanning tubing, comprising the steps of:
   scanning a tubing standard a first time with a tubing scanner to produce a first calibration scan;
   storing the first calibration scan;
   analyzing the first calibration scan and computing a transform based upon the first calibration scan;
   storing the transform;
   scanning tubing with the tubing scanner to obtain a plurality of tubing scan data;
   storing the tubing scan data;
   applying the transform to the tubing scan data to produced transformed tubing scan data;
   storing the transformed tubing scan data; and
   analyzing the transformed tubing scan data.

8. The method of claim 7 further comprising:
   scanning the tubing standard a second time with a tubing scanner after the scanning of the tubing is complete;
   comparing the first tubing standard scan with the second tubing scan; and
   optionally correcting the tubing scan data to account for differences between the first and second calibration scans.

9. The method of claim 8, further comprising scanning the tubing standard a plurality of times during the scanning of the tubing and computing the transform based upon all of the tubing standard scans.

10. The method of claim 7 further comprising flagging the tubing scan data if the difference between first and second tubing standard scans indicates that the tubing scanner has drifted out of calibration.

11. The method of claim 7 further comprising displaying the transformed tubing scan data.

12. The method of claim 7 further comprising determining the scan speed by comparing the first calibration scan data to a stored calibration scan.

13. The method of claim 7 further comprising:
   determining the location of collars on the tubing;
   recording the position of the collars;
   correlating the tubing scan data to a location on the tubing.

14. The method of claim 7 wherein the scanning of the tubing produces an analog signal.

15. The method of claim 14 further comprising converting the analog signal to a digital signal.

* * * * *